(12) United States Patent
Berberich (10) Patent No.: US 8,088,136 B2
(45) Date of Patent: Jan. 3, 2012

(54) MEDICAL INSTRUMENT FOR CUTTING TISSUE

(75) Inventor: Sascha Berberich, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 363 days.

(21) Appl. No.: 12/023,453

(22) Filed: Jan. 31, 2008

(65) Prior Publication Data
US 2008/0183201 A1   Jul. 31, 2008

(30) Foreign Application Priority Data

Jan. 31, 2007  (DE) .................. 10 2007 006 276

(51) Int. Cl.
A61B 17/32 (2006.01)
(52) U.S. Cl. ....................................... 606/180
(58) Field of Classification Search .................. 606/167, 606/180, 170–173, 179, 184, 185; 600/566, 600/567; 604/164.01, 164.07, 164.09, 164.11, 604/264
See application file for complete search history.

(56) References Cited

U.S. PATENT DOCUMENTS

| | | | | |
|---|---|---|---|---|
| 4,508,534 A * | 4/1985 | Garver et al. ................. | 604/111 |
| 4,667,837 A * | 5/1987 | Vitello et al. ................. | 215/228 |
| 4,685,472 A * | 8/1987 | Muto ............................. | 600/573 |
| 4,815,462 A * | 3/1989 | Clark ............................ | 606/170 |
| 5,282,821 A * | 2/1994 | Donahue ....................... | 606/170 |
| 5,287,845 A | 2/1994 | Faul et al. ......................... | 128/7 |
| 5,364,395 A * | 11/1994 | West, Jr. .......................... | 606/46 |
| 5,492,527 A | 2/1996 | Glowa et al. | |
| 5,665,101 A | 9/1997 | Becker et al. | |
| 5,741,287 A * | 4/1998 | Alden et al. ................... | 606/170 |
| 6,958,071 B2 | 10/2005 | Carusillo et al. ............... | 606/180 |
| 7,150,747 B1 * | 12/2006 | McDonald et al. ............. | 606/45 |
| 2004/0147909 A1 | 7/2004 | Johnston et al. | |
| 2005/0011855 A1* | 1/2005 | Zapata .......................... | 215/252 |
| 2005/0159767 A1 | 7/2005 | Adams et al. | |
| 2006/0025792 A1* | 2/2006 | Gibson et al. .................. | 606/170 |
| 2006/0212060 A1* | 9/2006 | Hacker et al. ................. | 606/180 |
| 2007/0016237 A1 | 1/2007 | Smith ............................ | 606/170 |
| 2007/0260263 A1* | 11/2007 | Case et al. ..................... | 606/108 |
| 2008/0300638 A1* | 12/2008 | Beardsley et al. ............. | 606/306 |

FOREIGN PATENT DOCUMENTS

| | | |
|---|---|---|
| DE | 26 37 747 | 2/1978 |
| DE | 41 01 472 | 7/1992 |
| EP | 1 166 722 | 1/2002 |
| WO | 9745054 A2 | 12/1997 |

OTHER PUBLICATIONS

European Search Report; EP 08 00 1608; Mar. 11, 2010; 4 pages.

* cited by examiner

*Primary Examiner* — Ryan Severson
*Assistant Examiner* — David Eastwood
(74) *Attorney, Agent, or Firm* — St. Onge Steward Johnston & Reens LLC (57) ABSTRACT

A medical instrument for cutting tissue has a tubular outer shaft, which comprises at least one window in the region of its distal end. The medical instrument further comprises a tubular inner shaft which is rotatable about a longitudinal axis and housed in the outer shaft and which has at its distal end a window arranged in the region of the at least one window of the outer shaft and provided with at least one cutting element. The medical instrument has a fixing element for unrotatably holding of the inner shaft relative to the outer shaft in a preset position. The fixing element is irreversibly detachable through rotational movement of the inner shaft.

11 Claims, 6 Drawing Sheets

MEDICAL INSTRUMENT FOR CUTTING TISSUE

CROSS-REFERENCE TO RELATED APPLICATION

The present application claims priority of German Patent Application No. 10 2007 006 276.3 filed on Jan. 31, 2007.

BACKGROUND OF THE INVENTION

The invention relates to a medical instrument for cutting tissue, comprising a tubular outer shaft, which has at least one window in the region of its distal end, further comprising a tubular inner shaft which is rotatable about a longitudinal axis and housed in the outer shaft and which has at its distal end a window arranged in the region of the at least one window of the outer shaft and provided with at least one cutting element.

Such instruments, also known as rotational cutting instruments or shavers, are used for example in minimally invasive surgery for separating tissue in a human or animal body.

A medical instrument known from U.S. Pat. No. 5,492,527 has a handgrip, connected on the distal side torque-proof to a tubular outer shaft. The outer shaft has a window at its distal end. Housed in the outer shaft is a tubular inner shaft, which likewise has a window at its distal end, in the region of the window of the outer shaft, with at least one cutting element. On its proximal side the inner shaft can be connected to drive means, for example an internal or external electric motor, for driving the inner shaft in rotation relative to the outer shaft about a longitudinal axis.

To remove tissue, the cutting element cooperates with the window of the outer shaft as the inner shaft revolves, such that the cutting element passes by the window and thus separates any tissue located to the side of the outer shaft. The separated tissue is suctioned in a proximal direction through the window via the inner shaft, to which a suction line is attached.

The initial position of the outer and inner shaft can be determined by the surgical procedure to be carried out, the preset position of both components being defined for example by the windows of the outer and inner shaft being arranged in a specific manner relative to one another. It may be preferred that the outer shaft and the inner shaft assume such a rotational positioning relative to one another that the window of the outer shaft is occluded by the distal end of the inner shaft, causing the inner shaft to be separated from the external environment. This is required in particular in procedures when the distal end of the outer shaft is inserted into the operating site with a suction line already attached and activated, to prevent sucking in uninvolved tissue or fluid, at the same time preventing both damage to the uninvolved tissue and also blockage of the distal end of the shaft. In other cases it can be desirable for the inner shaft to assume a rotational positioning relative to the outer shaft where the window of the outer shaft is opened to its maximum. Such a position of the inner shaft relative to the outer shaft is advantageous for example for interventions in the field of ear, nose and throat surgery, where the distal end of the outer shaft is not inserted deeply into the operating site and tissue or fluid is already being suctioned upon insertion to achieve better visual control for the surgeon.

The medical instrument known from the abovementioned U.S. Pat. No. 5,492,527 further has a holder provided between the outer shaft and the handgrip, with which holder the window of the outer shaft can be arranged torque-proof in a defined position relative to the handgrip. The holder is configured as two inter-engaging toothed rings with flat teeth, which can be pushed together by axial movement of a sleeve taking up the toothed rings. The outer shaft can be rotated about the longitudinal axis of the medical instrument relative to the handgrip in 15° increments, while the inner shaft remains in its starting position. When the medical instrument is in the operating state, the inner shaft rotates about the longitudinal axis, while the outer shaft is held in the previously set position.

A drawback to this medical instrument is that although the holder positions the outer shaft relative to the handgrip in a desired position, it does not hold the outer shaft and the inner shaft relative to one another in a preset rotational position. The inner shaft is borne to freely rotate in the outer shaft, resulting in the initial rotational positioning of both components, in particular the relative position of both windows to one another, being changed due to unwanted rotation of the inner shaft. This easily changed relative arrangement of the inner and outer shaft can lead to the abovedescribed unwanted suctioning of uninvolved tissue or fluid, in particular when the instrument is inserted into the body with activated suction line.

It is also disadvantageous that the outer shaft can describe an unwanted rotational movement, since the toothed rings are designed flat such that they can also be displaced relative to one another easily without axial shifting of the sleeve. The position of the outer shaft relative to the inner shaft can as a result be altered through slight inattention by the surgeon, for example by unwanted, manually forced rotating of the outer shaft, such that the outer shaft rotates relative to the handgrip and also relative to the inner shaft and the preset position of the respective components changes. Operating the medical instrument thus requires a high degree of attentiveness and caution on the part of the surgeon.

An added disadvantage is that the holder is structurally very complicated and results in high manufacturing costs for the medical instrument.

SUMMARY OF THE INVENTION

It is therefore an object of the present invention to improve the medical instrument of the type mentioned at the outset, by a structurally simple measure ensuring that the inner shaft maintains a predetermined rotational positioning relative to the outer shaft as the shaft is being inserted into the operating site.

According to the present invention, a medical instrument for cutting tissue is provided, comprising a tubular outer shaft having a distal end and having at least one first window arranged at the distal end, a tubular inner shaft arranged in the outer shaft and having a longitudinal axis and a distal end and being rotatable about the longitudinal axis, the tubular inner shaft having a second window arranged in a region of the at least one first window of the outer shaft, the second window being provided with at least one cutting element, and a fixing element for torque-proof holding of the inner shaft relative to the outer shaft in a preset position, the fixing element being irreversibly detachable through a rotational movement of the inner shaft relative to the outer shaft.

The medical instrument for cutting tissue according to the invention has a tubular outer shaft, housing a tubular inner shaft rotatable about a longitudinal axis. The outer shaft and the inner shaft in each case have at their distal end a window. The window of the inner shaft is arranged in the region of the window of the outer shaft and has at least one cutting edge. The medical instrument also has a fixing element, which holds the inner shaft relative to the outer shaft torque-proof in an initially preset position and which is irreversibly detachable by rotational movement of the inner shaft. In this way the medical instrument according to the invention advantageously has a mechanism with which the inner shaft is held torque-proof relative to the outer shaft as long until the inner shaft is set in rotation, for example by switching on the rotary drive, thus securely maintaining the preset position of the windows of the outer and inner shaft as the shaft is inserted into the operating site. If the preset rotational positioning is such that the outer window is closed, then the outer window remains firmly closed as the shaft is inserted into the operating site, so that if a suction stream is already applied it has no effect on the surrounding tissue through the outer window. Handling of the medical instrument is accordingly designed to be particularly user-friendly, since the surgeon does not need to pay attention to any unwanted changing of a preset position of the outer and inner shaft.

Also, releasing the connection between inner shaft and outer shaft is advantageously simple, since for release purposes only the inner shaft needs to be set in rotation by switching on the drive, without the operator having to be intervene in the release.

A further advantage of the medical instrument results from the fixing element being irreversibly detached when the instrument is started up, i.e. with rotation of the inner shaft relative to the outer shaft. As a result of this, the surgeon can already check prior to the operation as to whether the medical instrument is damaged and has to be exchanged for a new one with an as yet undetached fixing mechanism.

Due to its irreversibly detachable fixing element, the medical instrument according to the invention is suitable in particular as a disposable instrument. The fixing element can be made of breakable material, for example plastic, which breaks reproducibly in a defined area, i.e. at a nominal breaking point or along a nominal breaking line. It is likewise possible for the fixing element to be made from elastic, tearable material, for example rubber, which tears as a result of rotational movement of the inner shaft.

In a preferred embodiment of the invention, the fixing element connects a coupling element connected torque-proof to the outer shaft for connecting the outer shaft to a handgrip to a rotation transfer element connected torque-proof to the inner shaft for connecting the inner shaft to drive means.

The medical instrument further has a coupling element and a rotation transfer element, which is connected torque-proof to the outer shaft or respectively the inner shaft. The fixing element causes irreversibly detachable connection of both these components. The fixing element is thus advantageously not arranged directly on the inner and outer shaft, such that damage to both these components from breaking or tearing the fixing element is prevented, damage which can also have a disadvantageous effect on the relative rotational movement of the inner and outer shaft, and as a result on the cutting effect of the medical instrument.

In a further preferred embodiment of the invention, the fixing element is arranged on an external surface of the coupling element and of the rotation transfer element.

The advantage of this measure is that each and any arrangement of the inner shaft relative to the outer shaft is possible, since the fixing element can be provided at any position on the surface of the coupling element and of the rotation transfer element. During the manufacturing process, the fixing element can also be attached advantageously later to the external surface of both components, flexibly adapting the manufacture of the medical instrument to the respective operating requirements. Before using the medical instrument, the surgeon can also make a simple visual check as to whether the fixing element has a desired state suitable for use or is damaged.

In a further preferred embodiment of the invention, the fixing element is arranged at least partially peripherally on the coupling element and/or rotation transfer element.

The advantage of this measure is that, in contrast to the fixing element being arranged in local areas of the coupling and/or rotation transfer element, a particularly stable, torque-proof connection of the outer and inner shaft is effected.

In a further preferred embodiment of the invention, the coupling element and the fixing element are designed in one piece.

In a further preferred embodiment of the invention, the rotation transfer element and the fixing element are designed in one piece.

The advantage of these measures is that the respective components can be made in a single production step. This results in particularly rapid and at the same time cost-effective production of the medical instrument. In particular, the coupling element, the fixing element and the rotation transfer element can be designed in one piece.

In a further preferred embodiment of the invention, the fixing element has at least one oblong web which breaks, at least one nominal breaking point, due to rotational movement of the inner shaft.

This measure advantageously permits a structurally particularly simple and cost-effective embodiment of the fixing element, which guarantees stable torque-proof connection of the outer and inner shaft and can break in a defined area as a result of torsional and shearing forces occurring upon rotational movement of the inner shaft. In particular, it is an advantage for the fixing element to break at a nominal breaking point, thus preventing the fixing element from splitting into tiny fragments, which could remain inside the medical instrument and hinder the relative rotation of the outer and inner shaft.

In a further preferred embodiment of the invention, the at least one web is arranged along the longitudinal axis.

The advantage of this measure is that, due to the arrangement of the web parallel to the longitudinal axis, the connection of the coupling element to the rotation transfer element is equally stable against minor torques in both directions of rotation, thus preventing unwanted detaching of the web.

In an alternative preferred embodiment of the invention, the fixing element has a ring, which breaks along a nominal breaking line due to the rotational movement of the inner shaft.

This measure advantageously constitutes a further cost-effective and simple construction of the fixing element, which likewise ensures a particularly stable connection of the coupling element to the rotation transfer element due to the ring being arranged fully peripheral, thus preventing unwanted rotation of the inner shaft relative to the outer shaft. The ring can be irreversibly detached by breaking along a nominal breaking line.

In a further preferred embodiment of the invention, the medical instrument has a position indicator for aligning the inner shaft relative to the outer shaft in the preset position, the position indicator being arranged in alignment with the fixing element.

The position indicator serves to align the rotation transfer element and the coupling element, i.e. the inner shaft and the outer shaft, relative to one another during manufacture of the medical instrument. The arrangement of the respective components can advantageously be checked afterwards by the surgeon, so that, before the procedure is carried out, any deviation in the arrangement of the components is spotted and the medical instrument can be exchanged for another.

In a further preferred embodiment of the invention, the position indicator is arranged on the external surface of the coupling element.

This measure advantageously permits a possible arrangement of the position indicator visible to the surgeon, as compared to an arrangement for example on a surface of the rotation transfer element, since the coupling element is freely accessible and, unlike the rotation transfer element, cannot be covered by another component.

Further advantages and characteristics will emerge from the following description and the attached drawing.

It is understood that the abovementioned characteristics and those yet to be explained hereinbelow can be used not only in the combinations as specified, but also in other combinations or alone, without departing from the scope of the present invention.

BRIEF DESCRIPTION OF THE DRAWINGS

The invention will be described and explained in greater detail hereinbelow by way of some selected embodiments in conjunction with the attached drawing, in which.

DETAILED DESCRIPTION OF PREFERRED EXEMPLARY EMBODIMENTS

Figure 1:
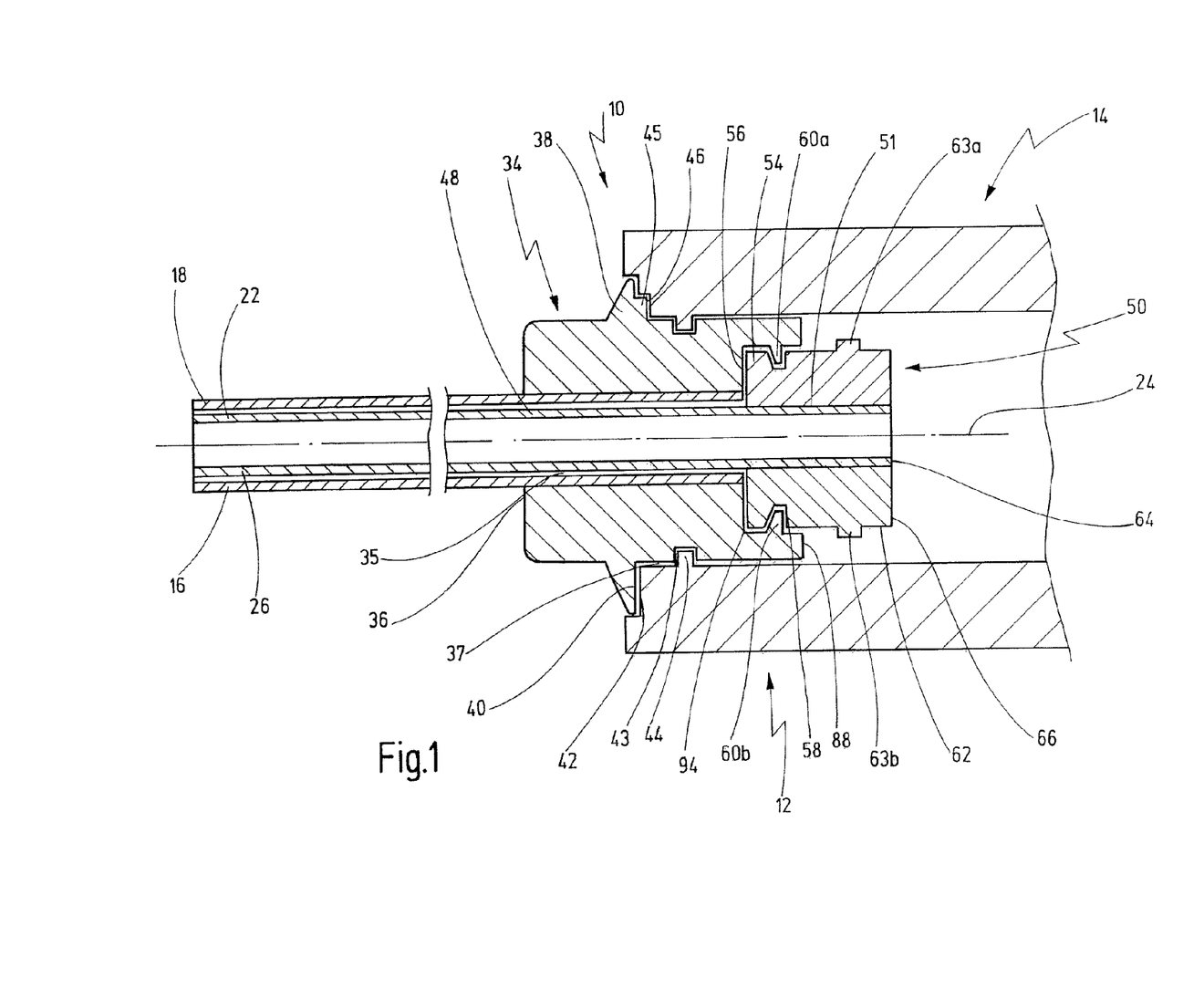
FIG. 1 shows a medical instrument for cutting tissue according to the present invention, in cross-section.
Figure 2:
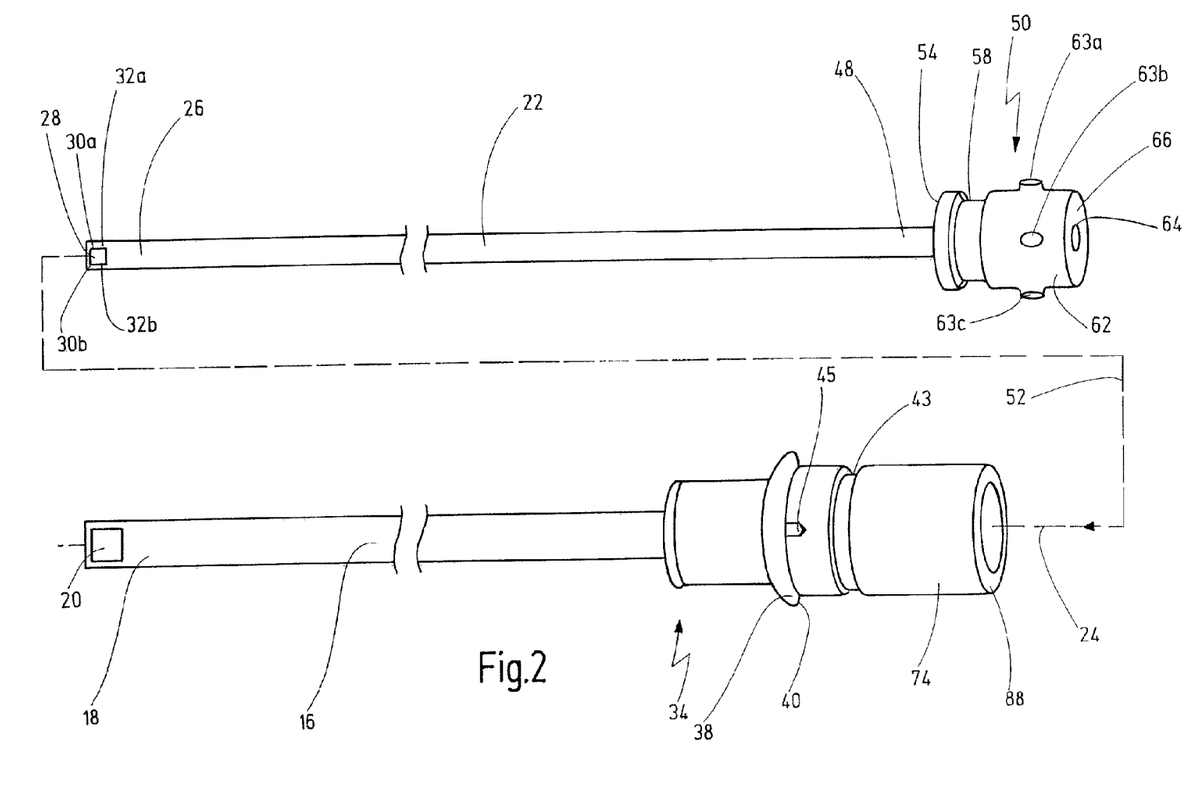
FIG. 2 is a perspective illustration of the medical instrument in FIG. 1 in an exploded view.

In FIG. 1, a medical instrument for cutting tissue is designated by the general reference numeral 10. Further details of the medical instrument 10 are depicted in FIGS. 2 to 6.

The medical instrument 10 is used for example in minimally invasive surgery for removing tissue in a human or animal body.

The medical instrument 10 has at its proximal end 12 a removable handgrip 14, on which an outer shaft 16 is arranged on the distal side. The outer shaft 16 is designed as a rigid hollow tube and at its distal end 18 has a semi-peripherally designed window 20. Housed in the outer shaft 16 is an inner shaft 22, likewise designed as a rigid hollow tube, designed to rotate about a longitudinal axis 24 of the medical instrument 10. In the region of its distal end 26 the inner shaft 22 has a window 28, which is arranged axially in the region of the window 20 of the outer shaft 16, such that the windows 20, 28 are at approximately the same axial level when the inner shaft 22 is in the received state (cf. FIG. 2). The window 28 of the inner shaft 22 is provided with at least one cutting element 30, illustrated here with two cutting elements 30a, b, which are provided to both sides on edges 32a, b of the window 28 arranged parallel to the longitudinal axis 24.

The inner shaft 22 can be set in rotation for removing tissue located to the side of the outer shaft 16, so that the cutting elements 30a, b pass by the window 20 of the outer shaft 16 and separate the tissue.

The outer shaft 16 and the inner shaft 22 are made of stainless steel with an appropriate wall thickness, so that both components have adequate rigidity against torsional forces occurring during the cutting procedure. A diameter of the outer shaft is in the region of a few millimetres and as a result is designed sufficiently small for the surgeon to have to make only a small incision in the outer skin of a patient before inserting the distal end 18 of the outer shaft 16 into the body.

The outer shaft 16 is connected torque-proof to a coupling element 34, via which the outer shaft 16 can be attached to the handgrip 14. In the case of the medical instrument 10 shown in FIGS. 1 to 6, the outer shaft 16 is covered with an inner surface 35 of an axially aligned borehole 36 of the coupling element 34. The coupling element 34 can be taken up via a plug connection at least partially in an opening 37 of the handgrip 14 on the distal side. For this, the coupling element 34 has a fully circumferential annular widened section 38, whereof the surface 40 arranged on the proximal side can be inserted into a corresponding annular depression 42 of the handgrip 14. The coupling element 34 also has a fully peripheral groove 43, in which an annular widened section 44 of the handgrip 14 engages. As a result of this, an axial displacement of the handgrip 14 and of the coupling element 34 is avoided. For torque-proof connection of the coupling element 34 to the handgrip 14, the coupling element 34 also has at least one web 45, which is arranged directly adjacent to the surface 40 of the annular widened section 38 and can be positively snap-locked in a corresponding seat 46 of the handgrip 14. The coupling element 34 can also have several webs 45, which can be inserted into respective seats 46 of the handgrip 14.

A proximal end region 48 of the inner shaft 22 is connected torque-proof to a rotation transfer element 50, by being stuck to an inner surface 51 of the rotation trans-fer element 50. In its received state the inner shaft 22 is placed along an arrow 52 illustrated in FIG. 2 in the outer shaft 16, so that a distal frontal face 54 of the rotation transfer element 50 rests on a proximal frontal face 56 of the coupling element 34. The rotation transfer element 50 also has a fully circumferential groove 58, in which peripherally arranged plug-in elements 60 of the coupling element 34 (two plug-in elements 60a, b illustrated in FIG. 1) engage positively, so that the rotation transfer element 50 and the coupling element 34 are arranged axially fixed, though freely rotatable to one another.

The coupling element 34 and the rotation transfer element 50 are made of plastic material, PVC for example.

In addition to this, drive means (not shown), for example an electromotor, can be attached to an external surface 62 of the rotation transfer element 50 and cause rotational movement of the rotation transfer element 50 relative to the coupling element 34, i.e. of the inner shaft 22 relative to the outer shaft 16. For this purpose, ellipsoid engaging elements 63, shown in FIG. 1 as two engaging elements 63a, b, in which a drive shaft of the drive means engages, are provided on the external surface 62 of the rotation transfer element 50 and are arranged substantially parallel to the longitudinal axis 24.

A suction line (not shown) can also be attached at a proximal end 64 of the inner shaft 22, which suction line engages for example via a plug-type connector in the proximal end 64 of the inner shaft 22. The proximal end 64 of the inner shaft 22 terminates with a proximally pointing frontal face 66 of the rotation transfer element 50, so that a distal end of the suction line can be arranged directly on the frontal face 66 of the rotation transfer element 50, creating a fluid-tight connection of the inner shaft 22 and suction line.

The medical instrument 10 further has a fixing element 68 which is irreversibly detachable by rotational movement of the inner shaft 22 and which in its undetached state holds the inner shaft 22 relative to the outer shaft 16 torque-proof in a preset position. The outer shaft 16 and the inner shaft 22 can be arranged for example such that the window 28 of the inner shaft 22 is arranged opposite the window 20 of the outer shaft 16, so that the window 20 of the outer shaft 16 is closed off by the distal end 26 of the inner shaft 22 (cf. FIG. 5). This arrangement of the windows 20, 28 is advantageous in particular within the scope of procedures in which the distal end 18 of the outer shaft 16 is inserted into a body orifice while the suction line is connected to the rotation transfer element 50 and activated. With respect to the outer shaft 16, the inner shaft 22 can likewise be arranged such that the window 20 of the outer shaft 16 is fully opened (cf. FIG. 3). This position of both windows 20, 28 may be preferred for surgical procedures in the field of ear, nose and throat medicine. Here the window 20 of the outer shaft 16 and the window 28 of the inner shaft 22 point in the same direction, so that fluid or tissue can also be suctioned from the operating site when the distal end 18 of the outer shaft 16 is inserted. It is likewise possible that the inner shaft 22 is held torque-proof relative to the outer shaft 16 in every possible position.

Figure 3:
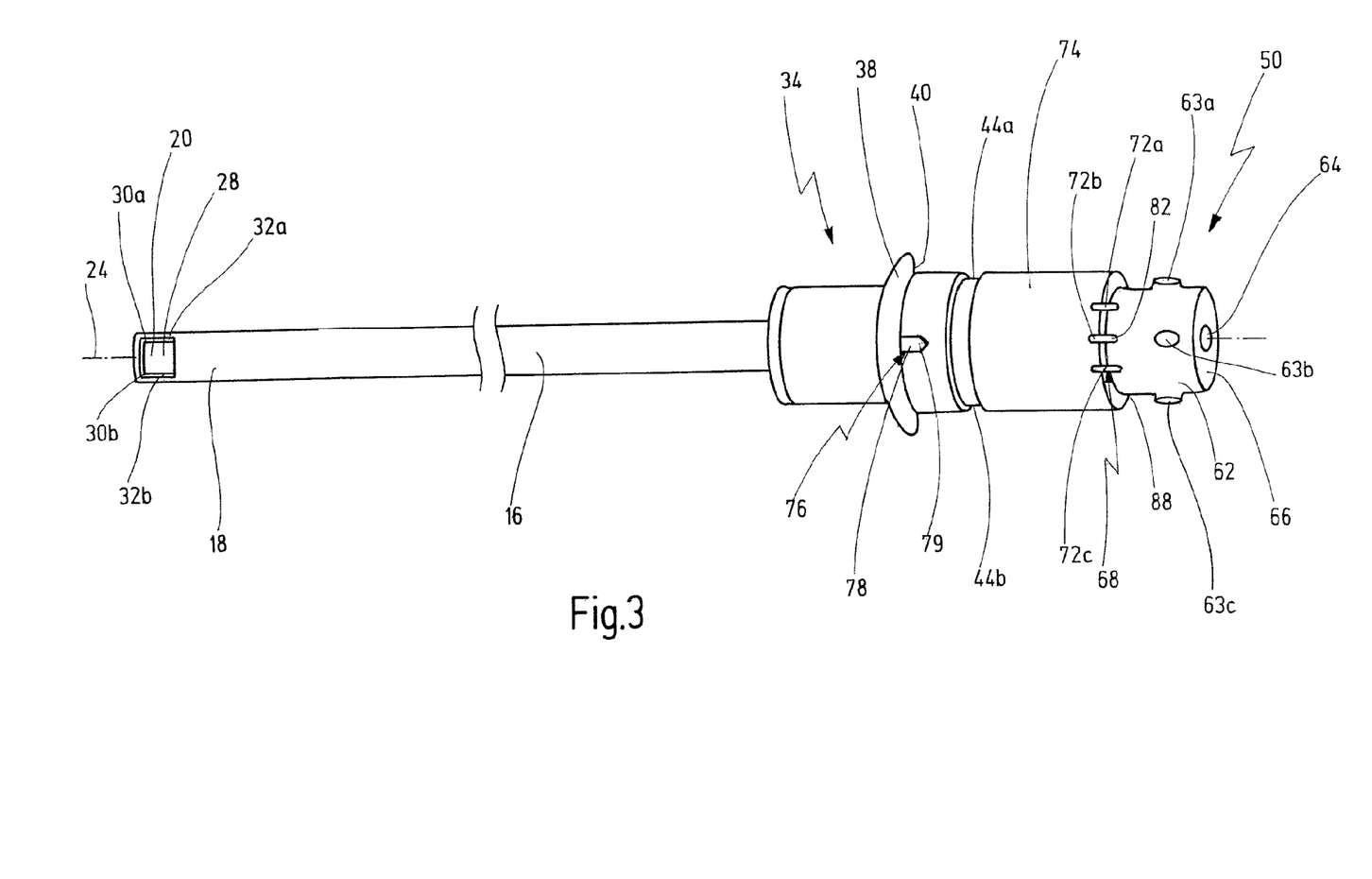
FIG. 3 is a further perspective illustration of the medical instrument in FIG. 1, which has a first embodiment of a fixing element.
Figure 4:
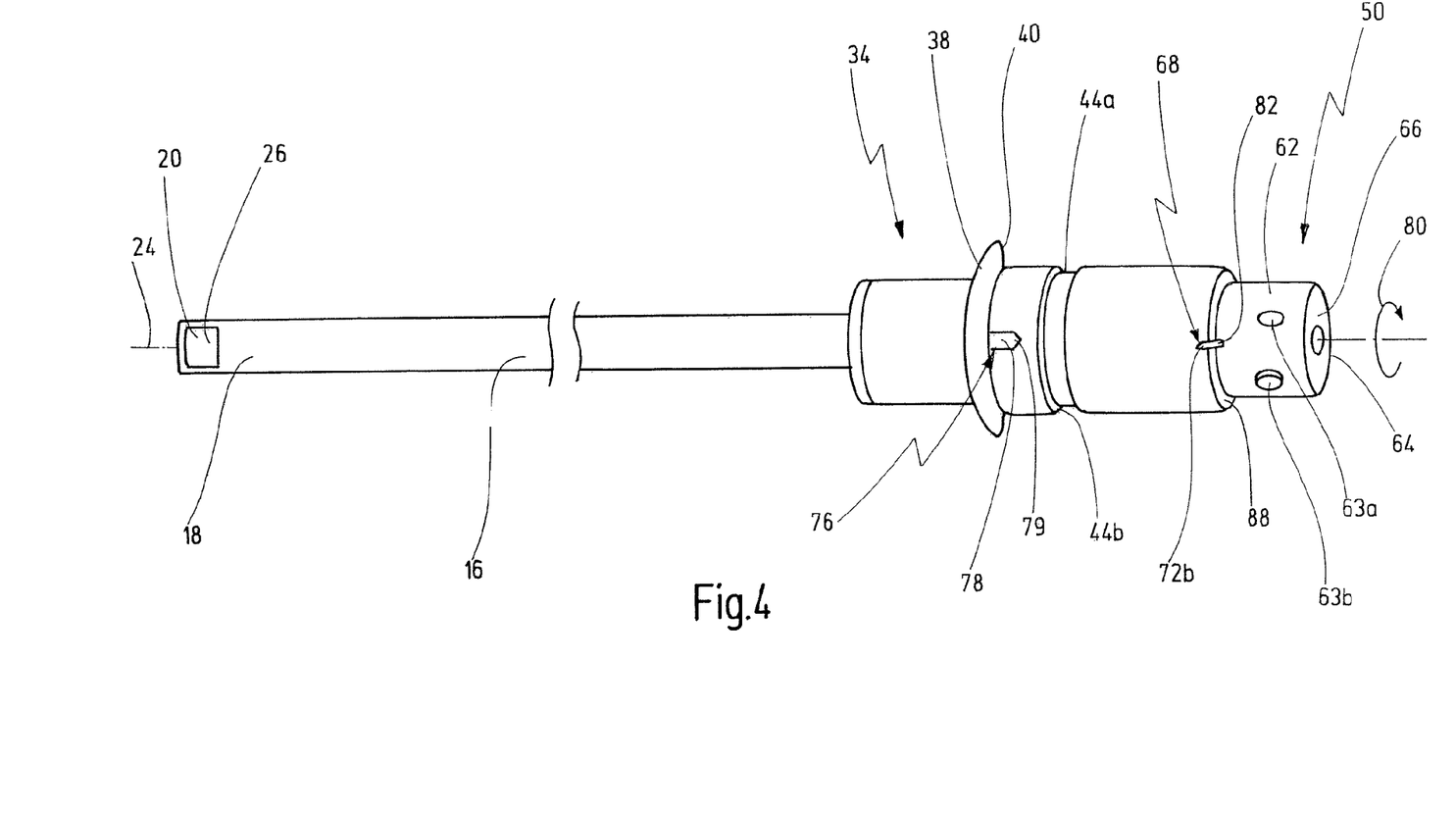
FIG. 4 is a further perspective illustration of the medical instrument in FIG. 3, the fixing element being irreversibly detached.

In a first embodiment illustrated in FIGS. 3, 4, the fixing element 68 has at least one oblong web 72 made of plastic, here three oblong webs 72a-c, which connect an external surface 74 of the coupling element 34 to the external surface 62 of the rotation transfer element 50. The plastic webs 72a-c are arranged along a periphery of the coupling element 34 and of the rotation transfer element 50 at regular intervals, for example in each case at 45° to the longitudinal axis 24.

The coupling element 34, the plastic webs 72a-c and the rotation transfer element 50 are designed in one piece by injection moulding when manufactured, such that the inner shaft 22 is arranged relative to the outer shaft 16 in the preset position imposed in each case. The three components can also be made by extrusion technology.

To align the relative position of the outer and inner shafts 16, 22 to one another and be able to check it later, the medical instrument 10 further has a position indicator 76, which is arranged in the form of a proximally pointing arrow 78 on the surface 74 of the coupling element 34 directly adjacent to the annular widened section 38. In an embodiment of the position indicator 76 illustrated in FIGS. 3 to 6, this corresponds to the web 45. During manufacture of the medical instrument 10, it is ensured that the plastic web 72b is arranged in alignment with for example a tip 79 of the arrow 78, so that, as shown in FIG. 3, the window 20 of the outer shaft 16 is opened. The plastic web 72b can also be colour-coded in particular and/or in addition a marking likewise in alignment with the position indicator 76 can be provided on the external surface 62 of the rotation transfer element 50, so that the relative arrangement of the outer and inner shafts 16, 22 can easily be adjusted and checked.

The position indicator 76 can likewise be placed on an area of the external surface 62 of the rotation transfer element 50 which is then for example visible when the coupling element 34 is not yet taken up in the handgrip 14. In place of the proximally pointing arrow 78, the position indicator 76 can be designed as a distally pointing arrow or as a small point distinguishable in colour from the coupling element 34 and rotation transfer element 50.

Figure 6:
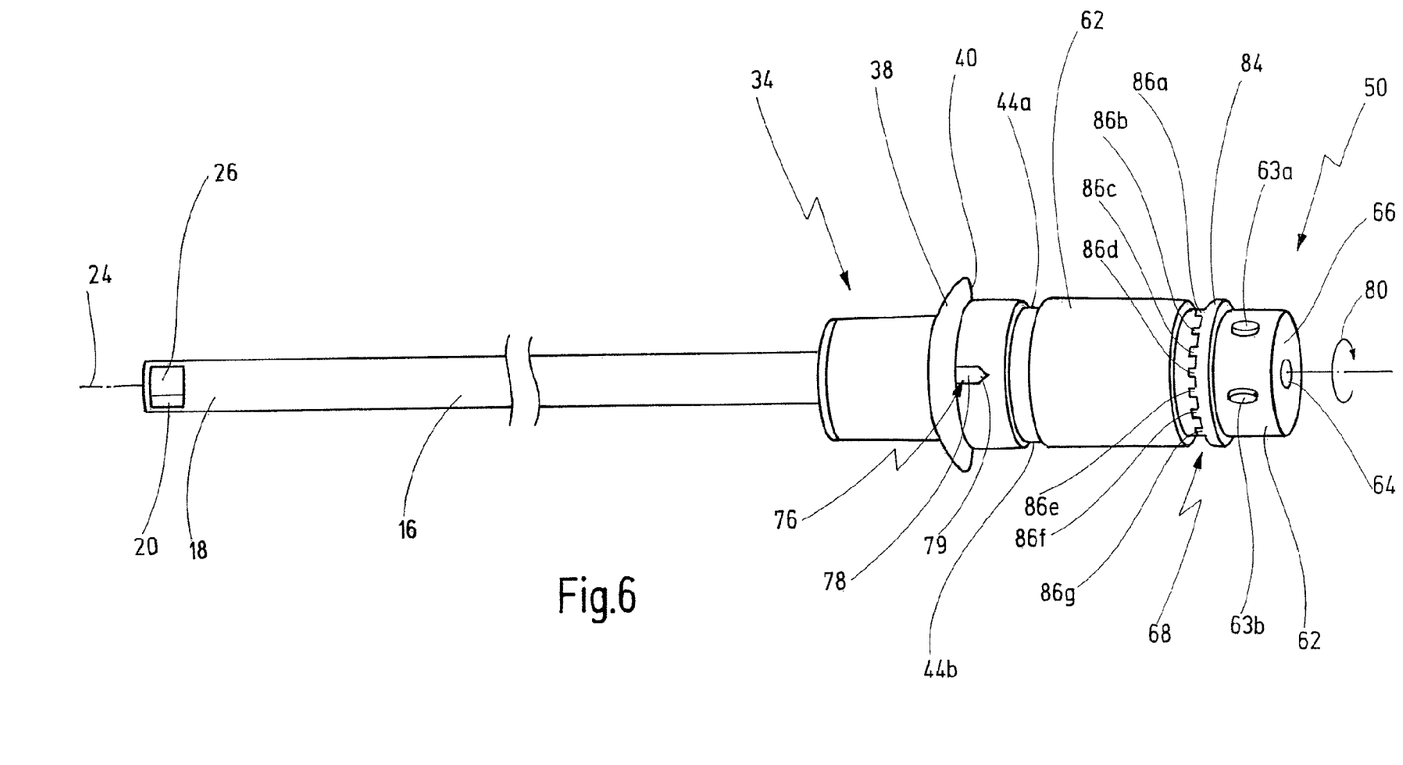
FIG. 6 is a further perspective illustration of the medical instrument in FIG. 5, the fixing element being irreversibly detached.

When the cutting elements 30a, b are started up, for example after the distal end 18 of the outer shaft 16 is inserted into the body orifice, the drive means cause rotational movement of the rotation transfer element 50 in the direction of an arrow 80 illustrated in FIGS. 4 and 6, which movement is transferred to the inner shaft 22. The outer shaft 16 remains in its position and does not rotate about the longitudinal axis 24. It is likewise possible for the inner shaft 22 to rotate counter to the direction of rotation indicated by the arrow 80.

The rotational movement of the inner shaft 22 generates torsional and shearing forces on the plastic webs 72a-c, which break at a nominal breaking point under the effect of sufficient force, as a result of which the torque-proof arrangement of the outer and inner shafts 16, 22 is irreversibly detached. As shown in FIG. 4, the plastic web 72b is broken off at its proximal end 82 from the surface 62 of the rotation transfer element 50, such that it is still attached only to the external surface 74 of the coupling element 34.

The webs 72a-c can also be perforated for example in their central region, in order to support their breaking in this defined area. This perforating acts here as a nominal breaking point of the fixing element 68.

Due to the irreversibly detachable fixing element 68, the medical instrument 10 is suitable in particular as a disposable instrument.

Figure 5:
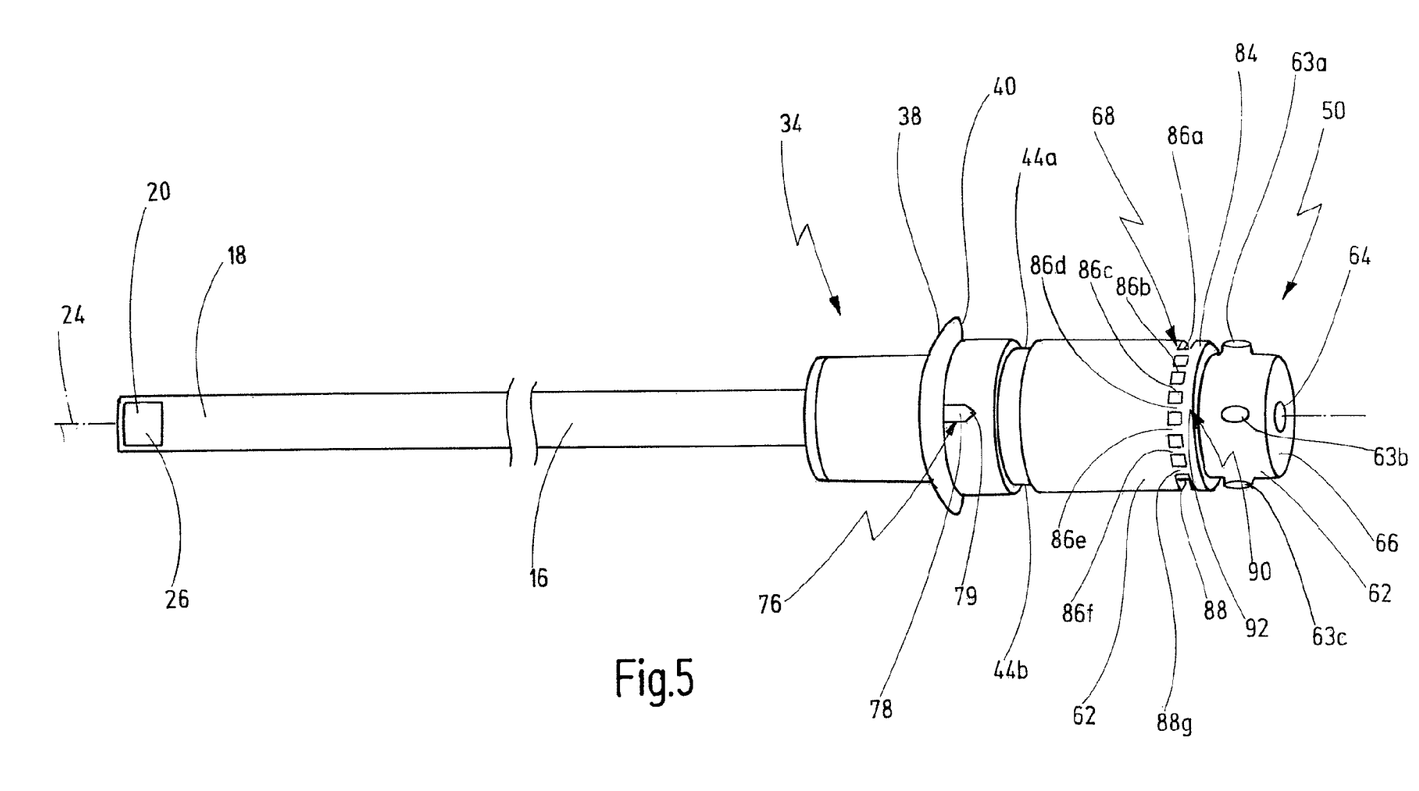
FIG. 5 is a further perspective illustration of the medical instrument in FIG. 1, which has a second embodiment of the fixing element.

In a further embodiment illustrated in FIG. 5, the fixing element 68 is designed as a fully peripheral plastic ring 84, which is connected via small plastic bridges 86, illustrated here as seven plastic bridges 86a-g, to a frontal face 88 on the proximal side of the coupling element 34. The plastic ring 84, the plastic bridges 86a-g and the coupling element 34 are injection-moulded in one piece.

The plastic ring 84 sits frictionally engaged on the external surface 62 of the rotation transfer element 50, so that the rotation transfer element 50 and the coupling element 34 are arranged torque-proof to one another in an idle state. As a result of this, the inner shaft 22 and the outer shaft 16 are arranged in such a position in which the distal end 26 of the inner shaft 22 seals off the window 20 of the outer shaft 16, as shown in FIG. 5. The position indicator 76 is arranged in alignment with a region 90 of the plastic ring 84 marked in particular by its colouring, here illustrated by a colour dot 92.

As shown in FIG. 6, the rotational movement of the inner shaft 22 along the arrow 80 causes rotation of the rotation transfer element 50 relative to the coupling element 34, so that torsional and shearing forces engage on the plastic bridges 86a-g. The ring 84 breaks away from the coupling element 34 under this force effect along the plastic bridges 86a-g, which define a nominal breaking line of the fixing element 68. The plastic ring 84 separated from the coupling element 34 remains in this position throughout the remaining time of the surgical procedure.

It is likewise possible that the fixing element 68 is made from flexible, tearable material, for example rubber, which is arranged between the external surface 62 of the rotation transfer element 50 and an inner surface 94 of the coupling element 34. The rubber tears as a result of a torque occurring upon the rotational movement and detaches the inner shaft 22 irreversibly from the outer shaft 16.

What is claimed, is:

1. A medical instrument for cutting tissue, comprising a tubular outer shaft having a distal end and having at least one first window arranged at the distal end, a tubular inner shaft arranged in the outer shaft and having a longitudinal axis and a distal end and being rotatable about the longitudinal axis, the tubular inner shaft having a second window arranged in a region of the at least one first window of the outer shaft, the second window being provided with at least one cutting element, and a fixing element for holding the inner shaft relative to the outer shaft in a preset rotational position, the fixing element being breakable through a rotational movement of the inner shaft about the longitudinal axis relative to the outer shaft so that once the fixing element is broken, the inner shaft is freely rotatable with respect to the outer shaft;

wherein said medical instrument further comprises a coupling element connected non-rotatably to the outer shaft for connecting the outer shaft to a handgrip, a rotation transfer element connected to the inner shaft for connecting the inner shaft to drive means, wherein the fixing element connects the coupling element with the rotation transfer element.

2. The medical instrument of claim 1, wherein the fixing element is arranged on an external surface of the coupling element and of the rotation transfer element.

3. The medical instrument of claim 1, wherein the fixing element is arranged at least partially peripherally on the coupling element.

4. The medical instrument of claim 1, wherein the fixing element is arranged at least partially peripherally on the rotation transfer element.

5. The medical instrument of claim 1, wherein the coupling element and the fixing element are designed in one piece.

6. The medical instrument of claim 1, wherein the rotation transfer element and the fixing element are designed in one piece.

7. The medical instrument of claim 1, wherein the fixing element has at least one oblong web which breaks, due to the rotational movement of the inner shaft, at least one nominal breaking point.

8. The medical instrument of claim 7, wherein the at least one web is arranged along the longitudinal axis.

9. The medical instrument of claim 1, wherein the fixing element has a ring, which breaks along a nominal breaking line due to the rotational movement of the inner shaft.

10. The medical instrument of claim 1, further comprising a position indicator for aligning the inner shaft relative to the outer shaft in the preset position, the position indicator being arranged in alignment with the fixing element.

11. The medical instrument of claim 10, wherein the position indicator is arranged on the external surface of the coupling element.

* * * * *